United States Patent
Pensler et al.

(10) Patent No.: US 9,616,217 B1
(45) Date of Patent: Apr. 11, 2017

(54) METHOD OF APPLYING ELECTROTHERAPY TO FACIAL MUSCLES

(71) Applicants: Jay Pensler, Chicago, IL (US); Christopher Robinson, Elmwood Park, IL (US); Alexander Pensler, Chicago, IL (US)

(72) Inventors: Jay Pensler, Chicago, IL (US); Christopher Robinson, Elmwood Park, IL (US); Alexander Pensler, Chicago, IL (US)

( * ) Notice: Subject to any disclaimer, the term of this patent is extended or adjusted under 35 U.S.C. 154(b) by 170 days.

(21) Appl. No.: 14/489,447

(22) Filed: Sep. 17, 2014

(51) Int. Cl.
  *A61N 1/00* (2006.01)
  *A61N 1/04* (2006.01)
  *A61N 1/36* (2006.01)

(52) U.S. Cl.
  CPC ....... *A61N 1/0456* (2013.01); *A61N 1/36003* (2013.01)

(58) Field of Classification Search
  CPC ............ A61N 1/36003; A61N 1/36014; A61N 1/0452
  USPC .......................................................... 607/48
  See application file for complete search history.

(56) References Cited

U.S. PATENT DOCUMENTS

| 2,842,136 A | 7/1958 | Browner |
| 6,801,808 B2 | 10/2004 | Lee |
| 2005/0107831 A1* | 5/2005 | Hill .................... A61H 23/0245 607/2 |
| 2010/0114240 A1* | 5/2010 | Guntinas-Lichius A61N 1/0526 607/48 |

* cited by examiner

*Primary Examiner* — Amanda Patton
*Assistant Examiner* — Philip C Edwards
(74) *Attorney, Agent, or Firm* — LaMorte & Associates, P.C.

(57) ABSTRACT

A system and method of exercising targeted muscles of the face using electrotherapy. An electrotherapy machine is provided that produces both burst mode oscillating current and biphasic current. Burst mode oscillating current is used to map positions for electrodes that cause contractions in specific regions of the targeted muscles. Biphasic current is used to map positions for electrodes that stimulate the buccal nerve branch and cause simultaneous contractions of the entire targeted muscles. After mapping burst mode oscillating current is directed from the electrotherapy machine to the first set of electrodes during a first period of time. Biphasic current is directed from the electrotherapy machine to a second set of electrodes during a second period of time that is subsequent to the first period of time. The cycles are repeated to cause concentric and eccentric contractions in the targeted muscles. The contractions exercise and tone the targeted muscles.

15 Claims, 4 Drawing Sheets

METHOD OF APPLYING ELECTROTHERAPY TO FACIAL MUSCLES

BACKGROUND OF THE INVENTION

1. Field of the Invention

In general, the present invention relates to methods of applying electrotherapy to the body to stimulate the contraction of targeted muscle groups. More particularly, the present invention relates to systems and methods of using electrotherapy on the muscle groups in the face.

2. Prior Art Description

It is well known that as a person ages, they lose muscle tone. As tone is lost in the muscles of the face, many of the muscles shrink and sag. This volume loss in conjunction with loss of tone causes parts of the face to appear sunken, sagged and in need of a face lift. Some people attempt to minimize the effects of aging by using various creams and ointments. However, these remedies only affect the skin and have no affects on the underlying muscle.

To alter the resting tone of the underlying muscle and deep tissues of the face, a person only has only a few options. A first option is to exercise those muscles of the face. A second option is to undergo a surgical facelift procedure. However, surgical facelifts are expensive and subject a person to the many dangers inherent in surgery. Surgical facelifts also have the disadvantages of having a long recovery time, result in new scars, and may producing results that look unnatural and/or unappealing. A third option is to have a medically approved filler injected into the deep tissues of the face. Injections while replacing volume to a degree do not increase resting tone of the musculature which would result in lifting the tissues.

Of the available options, the superior method for facial rejuvenation is to exercise of the muscles of the face. If the muscles of the face are exercised regularly, they will increase in both firmness and mass. As such, a person's face will naturally, without injections, appear fuller, firmer and less saggy. This restores a more youthful appearance. The primary shortcoming of exercising the muscles of the face is that it heretofore has been impossible to accomplish exercise to any significant degree. Several muscle groups extend across the face. It has not been feasible to perform exercises that isolate and contract the different muscle groups with enough intensity and resistance to produce a substantial change in muscle tone, volume or strength.

The muscles of the face can be exercised using electrotherapy, wherein the muscles are stimulated using an externally applied electric current. In the prior art, systems and methods have been developed to apply electrotherapy to the muscles of the face. Such prior art systems and methods are exemplified by U.S. Pat. No. 2,842,136 to Browner and U.S. Pat. No. 6,801,808 to Lee. However, such prior art devices have not found commercial success because they share an inherent problem. In the face, there are numerous nerves and muscles groups. Every person has a slightly different anatomy which places those nerves and muscles in slightly different positions on the face. As such, it has not been possible to create a product that will operate properly on all people in the specific region required. Rather, prior art devices tend to work properly on only a small insignificant subset of people.

In prior art electrotherapy systems, the electrodes are merely placed indiscreetly on the skin over any number of muscles that are desired to be contracted. However, placing electrodes in such a position may have the unintended effect of stimulating other nerves and muscles. For example, many of the muscles of the face overlap the masseter muscle, which is the primary muscle for closing the jaw. If electrotherapy is applied to the face, it can easily cause contraction of the masseter. This can cause the jaw to clench and cause pain, tooth damage and/or injury to the tongue. In addition, an uncoordinated contraction of a large group of facial muscles is in itself very painful and of no use for the purpose described below.

A need therefore exists for a system and method for applying electrotherapy to the muscles of the face that can be customized to the anatomy of an individual so as not to cause pain, yet to efficiently enhance targeted muscles. This need is met by the present invention as described and claimed below.

SUMMARY OF THE INVENTION

A novel technique is described to engage specific muscles of the face in order to significantly engage and stimulate those muscles employing electrotherapy and eccentric lengthening to achieve considerable clinical gains in directed regions of the face. For the electrotherapy component described, two electrodes are applied to the face over a specific muscle. A Russian electric current is then passed between the electrodes. The electric current causes the muscle to contract. By cycling the electric current, the muscle can be repeatedly caused to contract and relax. This primary stimulation results in muscle specific hypertrophy of a specific component of the muscle. An example of primary targeted stimulation would be current directed to the angular head of the Levator Labii Superioris muscle. Following application of the Russian current to the specific component of the muscle the facial nerve to the region is mapped and stimulated resulting in secondary stimulation of the entire muscle via the nerve and then sequentially the neighboring supporting muscles. During the sustained contraction of the targeted muscle or muscles via the facial nerve they are actively lengthened via an eccentric contraction. The direct targeted stimulation and subsequent, secondary stimulation and lengthening results in muscle specific hypertrophy and increased resting tone. The combined result of the process will be a strengthened and enlarged targeted muscle which lifts and restores volume to a specific region of the face.

An electrotherapy machine is provided that is capable of producing both burst mode oscillating current and biphasic current. The patient's face is mapped using the electrotherapy machine. Burst mode oscillating current is used to map positions for electrodes that cause contractions in the targeted muscles without causing pain or significant contractions in untargeted muscles. Biphasic current is used to locate positions for electrodes that stimulate the buccal nerve branch of the facial nerve and cause simultaneous contractions of the targeted muscles.

A first set of electrodes is applied to select positions proximate the targeted muscles. Likewise, a second set of electrodes is applied to the face in selected positions proximate the buccal nerve branch that controls said targeted muscles.

Burst mode oscillating current is directed from the electrotherapy machine to the first set of electrodes during a first period of time. Biphasic current is directed from the electrotherapy machine to a second set of electrodes or alternatively repositioned first set electrodes during a second period of time that is subsequent to the first stimulation. The two independent cycles are designed in a manner to facilitate concentric and then eccentric contractions in the targeted muscles. The first set of electrical pulses stimulates a specific region of the targeted muscle directly which lies between and below the electrodes. The remaining portion of the muscle that lies outside of the treatment zone is not stimulated. The second set of pulses uses a different type of current to optimize stimulation of the facial nerve to the specific musculature to stimulate the entire muscle. The contractions decrease the length of the muscle providing slight muscular enhancement. Once the targeted muscles are actively contracting which shortens the muscles, the patient actively applies an opposing force. The opposing force significantly lengthens the contracted muscles to provide an eccentric contraction. The combination of concentric and eccentric contractions of the entire selected musculature substantially strengthens, hypertrophies and tones the targeted muscles.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention electrotherapy system and methodology can be used to exercise different muscles of the face, such as the muscles of the forehead, the embodiment illustrated shows the electrodes being used to cause controlled contractions primarily in the muscle groups under the cheeks. This illustrated application is merely demonstrative and should not be considered a limitation when interpreting the scope of the appended claims. The various electrodes can be used in different places to cause contractions in different muscle groups, as will be explained.

Figure 1:
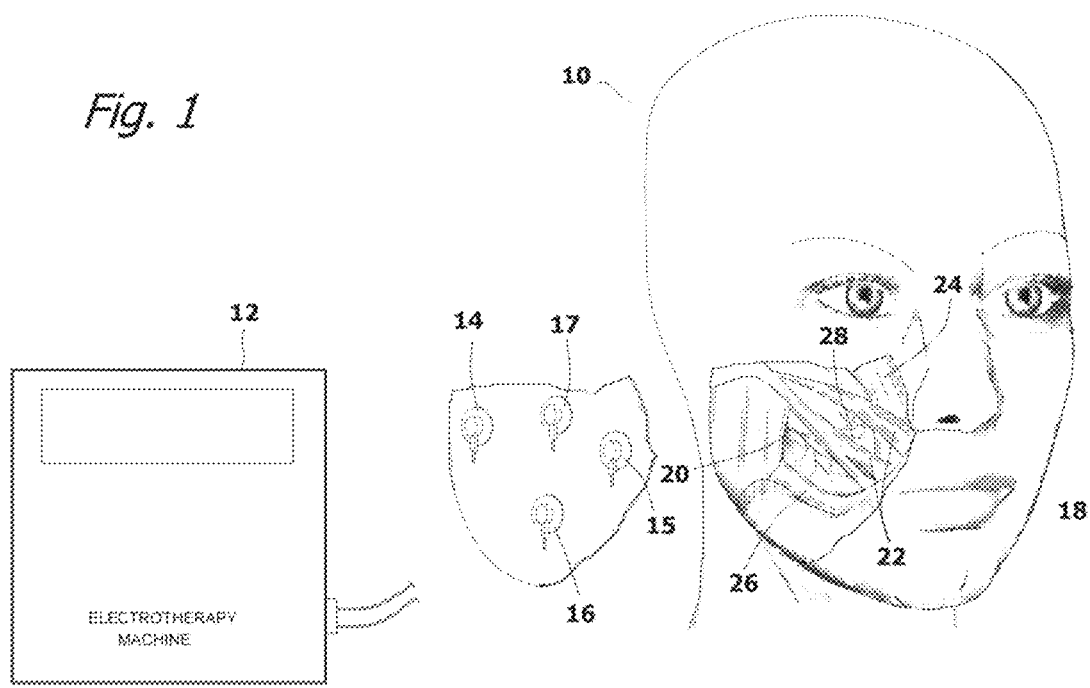
FIG. 1 is a fragmented view of a face shown in conjunction with the hardware needed to perform the claimed methodology.

Referring to FIG. 1, a head 10 is shown in conjunction with an electrotherapy machine 12. Electrotherapy machines are commercially available under a variety of brand names such as Chattanooga®. The electrotherapy machine 12 is capable of generating various controlled currents that are forwarded to various electrodes 14, 15, 16, 17. The electrodes 14, 15, 16, 17 can be attached to the skin of the face 18 at any desired points. The electrotherapy machine 12 is capable of generating both burst mode oscillating current and biphasic current. Burst mode oscillating current is often referred to as "Russian current" and consists of a medium frequency polyphasic AC waveform with burst modulations. There are typically 50 bursts per second with 50 pulses per burst. The burst mode oscillating current is applied between the first and second electrodes 14, 15. The biphasic current is applied between the third and fourth electrodes 16, 17 for the reasons later explained.

The muscle groups under the cheeks are primarily controlled by the facial nerve 20. The muscle groups under the checks include the zygomaticus minor and major 22, the levator labii superioris (and levator labii superioris alaeque nasi) 24 and the risorius and buccinator 26. The facial nerve 20 exits the skull via the stylomastoid foramen, which is behind the external auditory canal. The facial nerve 20 extends medially under the ear and into the cheek. The facial nerve 20 then divides into various branches 28, which include the temporal, zygomatic, buccal, mandibular and cervical branches. The size and location of these various branches 28 change significantly from individual to individual.

Figure 2:
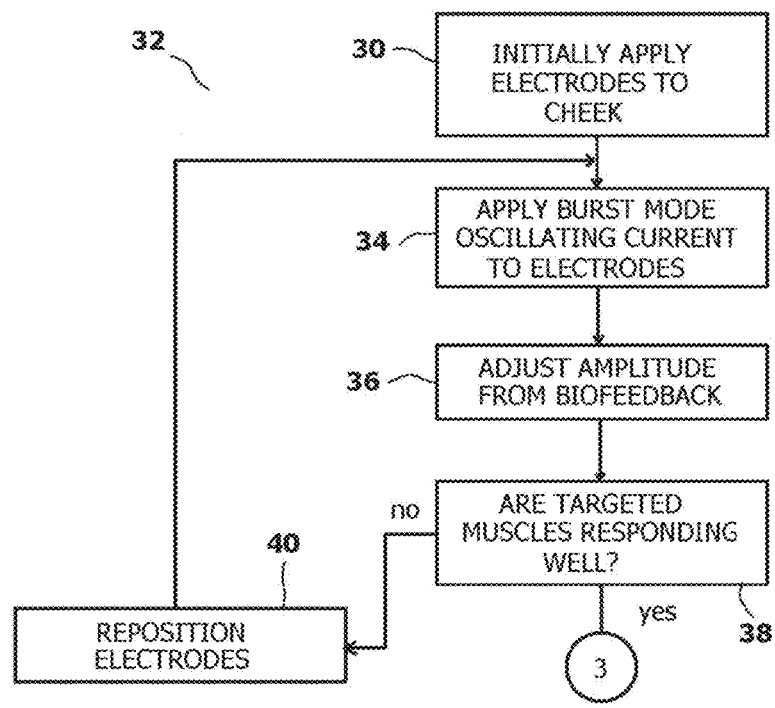
FIG. 2 is a block diagram showing the methodology of mapping the targeted muscles.
Figure 3:
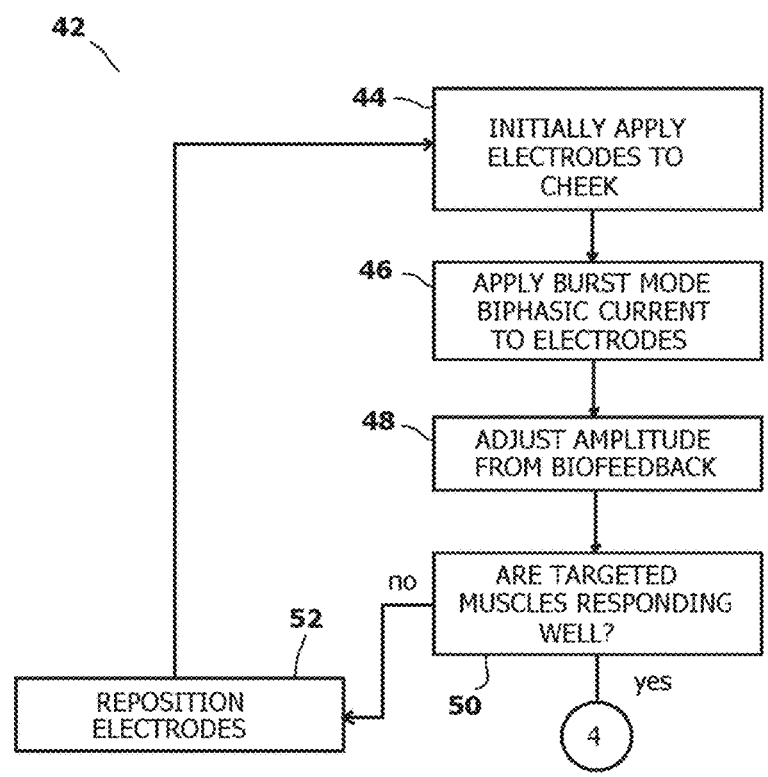
FIG. 3 is a block diagram showing the methodology of mapping the nerve branch that serves the targeted muscles.

Referring to FIG. 2 and FIG. 3, in conjunction with FIG. 1, it can be seen that the first two electrodes 14, 15 from the electrotherapy machine 12 are applied to the face 18 in the area of the cheek. See Block 30. The first electrode 14 is placed approximately 5 millimeters above, and anterior to, the external auditory canal. The second electrode 15 is initially placed approximately 4.0 centimeters in fermedial towards the corner of the lip, just lateral to the nasal labial fold. During placement, care is taken to be certain the placement of the second electrode 15 is lateral to the mid-pupillary line to ensure that the trigeminal maxillary branch of the facial nerve 20 will not be directly stimulated by the second electrode 15. In the shown application, the first electrode 14 is the negative electrode. The second electrode 15 is the positive electrode.

Once the first two electrodes 14, 15 are initially applied, a first mapping procedure 32 is performed to determine the best positions for the electrodes 14, 15 when receiving burst mode oscillating current (a.k.a. Russian current). In the first mapping procedure 32, burst mode oscillating current is applied to the electrodes 14, 15 in their initial positions. See Block 34. Treatment amplitude is determined from patient biofeedback. See Block 36. The patient is instructed to tell the technician when they initially feel the stimulation. The technician then slowly increases the amplitude in 0.1 mA increments until the level of stimulation is as high as can be comfortably tolerated by the patient. The typical settings range from 5.0 mA cc up to 20.0 mA cc.

During amplitude calibration, the technician visually and tactilely assesses feedback to confirm that the desired musculature is being stimulated. For a youthful appearance in the face, the muscles most typically desired for stimulation are the levator labii superioris and levator labbi superioris alaeque nasi) 24, the risorius 26 and the zygomaticus 22, which include the zygomaticus minor and zygomaticus major muscles. Thus, these muscle groups should contract when the burst mode oscillating current is applied. If good contractions are not obtained from the initial placement of the electrodes 14, 15, then the technician rearranges the electrodes 14, 15. See Block 38 and Block 40. The electrodes 14, 15 are repositioned using experienced trial and error to find positions where the targeted muscles contract well without any significant adverse side effects. To recognize adverse side effects, the patient is instructed to perform eccentric and concentric contractions of the face muscles in concert with the stimulation. This will make the patient cognizant of any pain or discomfort. From this first mapping procedure 32, the technician can determine where to place the first and second electrodes 14, 15 so that the targeted muscles contract well under burst mode oscillating current without causing pain to the patient and without causing undue contractions of non-targeted muscle groups, such as the masseter and buccinator.

Referring to FIG. 3 in conjunction with the earlier figures, it can be seen that once the first mapping procedure 32 is completed for the burst mode oscillating current, a second mapping procedure 42 is performed. The purpose of the second mapping procedure 42 is to locate the nerve branches 28 in the affected area. The goal is to locate the buccal branch among the various nerve branches 28. To locate the buccal nerve branch, the current produced by the electrotherapy machine 12 is altered to biphasic. The third and fourth electrodes 16, 17 are then applied to the cheek over where the buccal branch is expected to be in the anatomy of an average person. See Block 44. Biphasic current is then applied to the electrodes 16, 17. See Block 46. Treatment amplitude is determined from patient biofeedback. See Block 48. The patient is instructed to tell the technician when they initially feel the stimulation. The technician then slowly increases the amplitude in 0.1 mA increments until the level of stimulation is as high as can be comfortably tolerated by the patient. The typical settings range from 5.0 mA cc up to 20.0 mA cc.

The technician adjusts the position of the electrodes 16, 17 to points where the optimal stimulation of the buccal branch of the facial nerve is affected. The preferred parameters that are utilized for the biphasic current include a pulse duration of approximately 300 micro-seconds at a frequency of 35 Hz. The second mapping procedure 42 is done by trail and error using the visual and tactile confirmation of simultaneous contraction of all the targeted muscles controlled by the buccal branch of the facial nerve 20. See Block 50 and Block 52. The buccal branch of the facial nerve 20 controls the levator labii superioris, zygomaticus minor, zygomaticus major and the risorius. A technician knows the location of the buccal branch when he/she can create simultaneous contractions in all of these muscle groups by the application of the biphasic current. As the biphasic current is applied during the second mapping procedure 42, the patient is instructed to supplement the concentric contractions for one second and then to deliver sustained eccentric contractions at maximum effort for the residual of the biphasic pulse duration. This movement by the patient helps the technician identify the muscle groups and enables the patient to better identify pain tolerances.

At the end of both the first mapping procedure 32 and the second mapping procedure 42, the technician has collected biometric parameters that are unique to the patient. Those biometric parameters include:
1. the electrode location points on the patient that cause contractions using burst mode oscillating current;
2. the settings for the burst mode oscillating currents that are effective yet do not cause excessive pain and/or inadvertent side effects,
3. the location of the buccal nerve branch in the patient; and
4. the affective settings for stimulating the buccal nerve branch with biphasic current that do not cause excessive pain and/or inadvertent side effects.

Once the biometric parameters for a patient are known, those parameters are used to develop a treatment plan for the patient. The treatment plan is used on patients who need or want to increase the muscle mass and tone of some of the muscle groups of the face. Such patients can use the present invention methodology to treat one or more of the following:
1. decreased soft tissue mass or volume in the midface;
2. deep or deepening nasal labial folds;
3. inferior descent of the soft tissues of the midface;
4. increased soft tissue laxity of the midface;
5. deep or deepening marionette lines; and
6. Fitzpatrick Class 3 nasolabial wrinkles.

Figure 4:
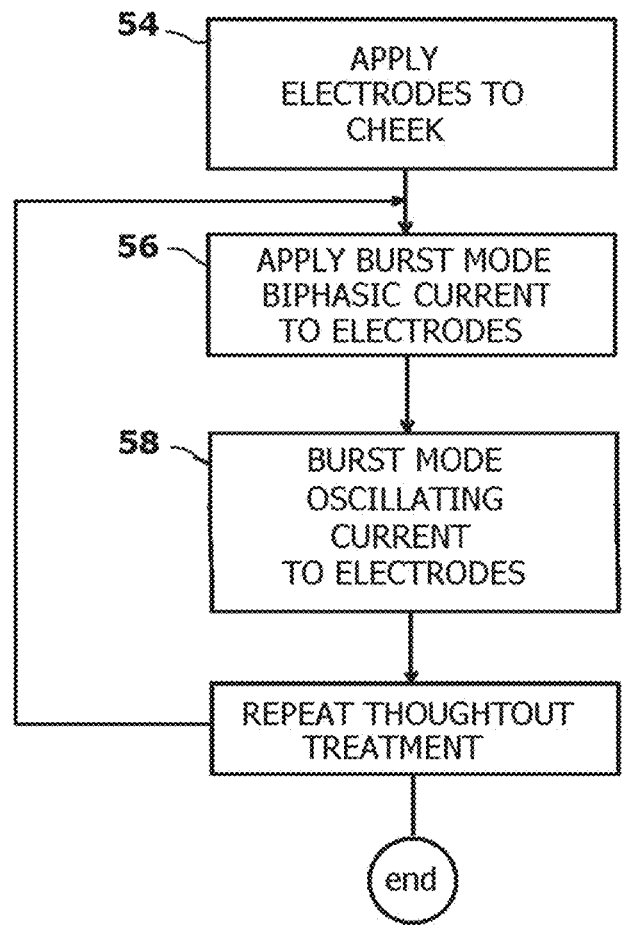
FIG. 4 is a block diagram showing the methodology of a treatment cycle.

Referring to FIG. 4 in conjunction will all earlier figures, it will be understood that when the patient comes in for a treatment session, the electrodes 14, 15, 16, 17 are placed on the patient's face in the positions previously mapped. See Block 54. In the first part of the treatment, burst mode oscillating current is then applied to the first and second electrodes 14, 15. See Block 56. The preferred initial treatment is set to a cycle time of 10 seconds on/20 seconds off to facilitate muscular recovery between treatment cycles. Subsequent treatments may be set to 10 seconds on/10 seconds off as the patient becomes accustomed to the procedure.

After the burst mode oscillating current procedure, the electrotherapy machine 12 is connected to the third and fourth electrodes 16, 17. The electrotherapy machine 12 is altered to provide biphasic current. The biphasic current is then applied to the electrodes 16, 17. See Block 58. Preferably, the pulse duration is set at 300 micro-seconds at a frequency of 35 HZ. The pulse duration can be increased gradually as the patient progresses through multiple treatments. The cycle time is initially is set to 10 seconds of stimulation followed by 20 seconds of rest time during the treatment. This rest interval may be decreased to 10 seconds in subsequent treatments. The treatment time is initially set to 10 minutes. This treatment time can be increased gradually up to 30 minutes.

From the above, it will be understood that the present invention methodology stimulates the facial musculature in two cycles using two different currents that are applied to different places. First, the use of burst mode oscillating current directly stimulates and strengthens targeted facial musculature. This current is applied directly to the targeted facial muscles. Following this initial procedure, the present invention methodology utilizes a biphasic current to directly stimulate the selected nerve branches to achieve contraction of the targeted facial muscles. This biphasic current is applied to the buccal branch of the facial nerve.

The present invention methodology stimulates the targeted facial muscles to vigorously contract and exercise those muscles to reduce or reverse muscle atrophy. The application of both burst mode oscillating current to the muscles and the application of biphasic current to the muscle nerve produces both concentric and eccentric contractions within the targeted muscles. The activity builds up the resting tone of the facial muscles lifting the soft tissues of the face secondarily to the increased muscle tone and the increased muscular volume. This produces a more youthful appearance of the face.

It will be understood that the embodiment of the present invention that is illustrated and described is merely exemplary and that a person skilled in the art can make many variations to that embodiment. For instance, the same methodology can be used to exercise other facial muscle groups, such as the frontalis and procerus muscles of the forehead. All such embodiments are intended to be included within the scope of the present invention as defined by the claims.

What is claimed is:
1. A method of exercising targeted muscles of the face using electrotherapy, said method comprising the steps of:
providing an electrotherapy machine capable of producing both burst mode oscillating current and biphasic current;
applying a first set of electrodes to the face in first positions proximate said targeted muscles;
applying a second set of electrodes to the face in second positions, different from said first positions, that are proximate a nerve that controls said targeted muscles;
connecting said electrotherapy machine to said first set of electrodes;
directing said burst mode oscillating current from said electrotherapy machine to said first set of electrodes during a first period of time, therein causing contractions in said targeted muscles during said first period of time;
connecting said electrotherapy machine to said second set of electrodes; and
directing said biphasic current from said electrotherapy machine to said second set of electrodes during a second period of time that is subsequent to said first period of time, wherein said biphasic current stimulates said nerve that controls said targeted muscles.

2. The method according to claim 1, wherein said step of directing said burst mode oscillating current and said step of directing biphasic current are repeated in succession throughout a predetermined treatment cycle.

3. The method according to claim 1, wherein said targeted muscles are selected from a group consisting of levator labii superioris, zygomaticus and risorius.

4. The method according to claim 1, wherein said first positions are determined by manipulating said first set of electrodes through a variety of positions and transmitting a burst mode oscillating current through said first set of electrodes, wherein said first positions are positions from said variety of positions that cause good contractions of said targeted muscles without significant contractions of muscles other than said targeted muscles.

5. The method according to claim 1, wherein said second positions are determined by manipulating said second set of electrodes through a variety of positions and transmitting a biphasic current through said second set of electrodes, wherein said second positions are positions from said variety of positions that cause simultaneous contractions of said targeted muscles without significant contractions of muscles other than said targeted muscles.

6. The method according to claim 1, wherein said step of directing said burst mode oscillating current from said electrotherapy machine to said first set of electrodes includes applying said burst mode oscillating current at a selected amplitude, wherein said amplitude is determined by biofeedback.

7. The method according to claim 1, wherein said step of directing said biphasic current from said electrotherapy machine to said second set of electrodes includes applying said burst mode oscillating current at a selected amplitude, wherein said amplitude is determined by biofeedback.

8. A method of exercising muscles of the face by electrical stimulation of targeted muscles and a nerve that serves the targeted muscles, said method comprising the steps of:

applying a first set of electrodes to the face in first positions proximate said targeted muscles;
applying a second set of electrodes to the face in second positions, different from said first positions, that are proximate said nerve that serves said targeted muscles;
sending burst mode oscillating current through said first set of electrodes during a first period of time, to cause contractions in said targeted muscles during said first period of time;
sending biphasic current through said second set of electrodes during a second period of time, to stimulate said nerve and cause contractions in said targeted muscles during said second period of time.

9. The method according to claim 8,
wherein said first period of time and said second period of time occur alternately and repeatedly.

10. The method according to claim 8, wherein said burst mode oscillating current and said biphasic current are both generated by an electrotherapy machine.

11. The method according to claim 8, wherein said targeted muscles are selected from a group consisting of levator labii superioris, zygomaticus and risorius.

12. The method according to claim 8, wherein said first positions are determined by manipulating said first set of electrodes through a variety of positions and transmitting burst mode oscillating current through said first set of electrodes, wherein said first positions are positions from said variety of positions that cause good contractions of said targeted muscles without significant contractions of muscles other than said targeted muscles.

13. The method according to claim 8, wherein said second positions are determined by manipulating said second set of electrodes through a variety of positions and transmitting biphasic current through said second set of electrodes, wherein said second preselected positions are positions from said variety of positions that cause good simultaneous contractions of said targeted muscles without significant contractions of muscles other than said targeted muscles.

14. The method according to claim 8, further including the step of determining an amplitude for said burst mode oscillating current using biofeedback.

15. The method according to claim 8, further including the step of determining an amplitude for said biphasic current using biofeedback.

* * * * *